US012714673B2

(12) United States Patent
Enomura et al.

(10) Patent No.: US 12,714,673 B2
(45) Date of Patent: Aug. 25, 2026

(54) PLGA MICROPARTICLES, A SUSTAINED RELEASE FORMULATION THEREOF AND A PRODUCTION METHOD THEREOF

(71) Applicant: M. TECHNIQUE CO., LTD., Izumi (JP)

(72) Inventors: Masakazu Enomura, Izumi (JP); Kaeko Araki, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 1067 days.

(21) Appl. No.: 17/431,566

(22) PCT Filed: Mar. 14, 2019

(86) PCT No.: PCT/JP2019/010618
§ 371 (c)(1),
(2) Date: Aug. 17, 2021

(87) PCT Pub. No.: WO2020/183718
PCT Pub. Date: Sep. 17, 2020

(65) Prior Publication Data
US 2022/0133632 A1 May 5, 2022

(51) Int. Cl.
*A61K 9/16* (2006.01)
*A61K 9/00* (2006.01)
(Continued)

(52) U.S. Cl.
CPC ............ *A61K 9/1647* (2013.01); *C08J 3/122* (2013.01); *C08J 2367/04* (2013.01)

(58) Field of Classification Search
CPC .. A61K 9/1647; A61K 9/0024; A61K 9/1694; A61K 9/10; A61K 47/34; C08J 3/122; C08J 2367/04
See application file for complete search history.

(56) References Cited

U.S. PATENT DOCUMENTS 5,480,656 A 1/1996 Okada et al.
5,643,607 A 7/1997 Okada et al.
(Continued)

FOREIGN PATENT DOCUMENTS

CN 102516809 B 4/2015
JP 2653255 B2 9/1997
(Continued)

OTHER PUBLICATIONS

International Search Report, issued in PCT/JP2019/010618, PCT/ISA/210, dated Jun. 4, 2019.
(Continued)

*Primary Examiner* — Trevor Love
*Assistant Examiner* — Janet Joseph
(74) *Attorney, Agent, or Firm* — Birch, Stewart, Kolasch & Birch, LLP

(57) ABSTRACT

Approximately spherical lactic acid-glycolic acid copolymer (PLGA) microparticles include a biologically active substance. An average volume-based particle diameter of the PLGA microparticles is 1 μm or more and 150 μm or less. A Reactive Span Factor (R.S.F.) of the PLGA microparticles is satisfied with formula (1): $0.1<(\text{R.S.F.})\leq 1.7$ formula (1), wherein an R.S.F. means (D90−D10)/D50; D90 is a particle diameter (μm) corresponding to the cumulative 90% by volume of the cumulative particle diameter distribution from the small particle side; D50 is a particle diameter (μm) corresponding to the cumulative 50% by volume of the cumulative particle diameter distribution from the small particle side; and D10 is a particle diameter (μm) corresponding to the cumulative 10% by volume of the cumulative particle diameter distribution from the small particle side.

5 Claims, 6 Drawing Sheets

(51) Int. Cl.

| | |
|---|---|
| ***A61K 9/10*** | (2006.01) |
| ***A61K 47/34*** | (2017.01) |
| ***C08J 3/12*** | (2006.01) |

(56) References Cited

U.S. PATENT DOCUMENTS

| | | | | |
|---|---|---|---|---|
| 5,814,342 | A | 9/1998 | Okada et al. | |
| 5,945,126 | A | 8/1999 | Thanoo et al. | |
| 9,211,510 | B2 | 12/2015 | Enomura | |
| 10,179,111 | B2 * | 1/2019 | Gottardi | A61K 31/496 |
| 2004/0032792 | A1 | 2/2004 | Enomura | |
| 2006/0134223 | A1 | 6/2006 | Yamada | |
| 2006/0266847 | A1 | 11/2006 | Enomura | |
| 2007/0059363 | A1 | 3/2007 | Lee et al. | |
| 2010/0155310 | A1 | 6/2010 | Enomura | |
| 2014/0341997 | A1 | 11/2014 | Kim et al. | |
| 2015/0209342 | A1 * | 7/2015 | Lu | A61K 31/192 514/569 |
| 2015/0352055 | A1 | 12/2015 | Asin et al. | |
| 2017/0035856 | A1 | 2/2017 | Wang et al. | |
| 2017/0239240 | A1 | 8/2017 | Vasisht et al. | |
| 2017/0260228 | A1 | 9/2017 | Kasuya et al. | |
| 2018/0085314 | A1 | 3/2018 | Morinaga et al. | |
| 2018/0117123 | A1 | 5/2018 | Wang et al. | |

FOREIGN PATENT DOCUMENTS

| | | | |
|---|---|---|---|
| JP | 2001-512461 | A | 8/2001 |
| JP | 2004-49957 | A | 2/2004 |
| JP | 2005-15476 | A | 1/2005 |
| JP | 2005-35994 | A | 2/2005 |
| JP | 2006-131577 | A | 5/2006 |
| JP | 2009-132871 | A | 6/2009 |
| JP | 4856752 | B2 | 1/2012 |
| JP | 2014-50843 | A | 3/2014 |
| JP | 2014-224114 | A | 12/2014 |
| JP | 2016-506923 | A | 3/2016 |
| JP | 2017-511371 | A | 4/2017 |
| JP | 2018-52922 | A | 4/2018 |
| KR | 10-1402734 | B1 | 6/2014 |
| WO | WO 2016/039359 | A1 | 3/2016 |
| WO | WO 2017/147285 | A1 | 8/2017 |

OTHER PUBLICATIONS

Chinese Office Action and Search Report for Chinese Application No. 201980093053.3, dated Nov. 1, 2022, with English translation.

Extended European Search Report for European Application No. 19919052.1, dated Sep. 22, 2022.

Korean Office Action for Korean Application No. 10-2021-7031247, dated May 28, 2024, with an English translation.

* cited by examiner

FIG. 1 q3 (%)

Relative particle amount 20 18 16 14 12 10 8 6 4 2 0

0.01 0.05 0.1 0.5 1 5 10 50 100 500

Particle diameter (μm)

PLGA MICROPARTICLES, A SUSTAINED RELEASE FORMULATION THEREOF AND A PRODUCTION METHOD THEREOF

TECHNICAL FIELD

The present inventions relate to lactic acid-glycolic acid copolymer (PLGA) microparticles, a sustained release formulation thereof and a production method thereof. The present inventions specifically relate to approximately spherical PLGA microparticles comprising a biologically active substance, a sustained release formulation thereof and a production method thereof.

BACKGROUND ART

Recently, a microsphere or nanosphere has attracted attention as a sustained release formulation of a medicine containing a biologically active substance or the like. A microsphere generally refers to a formulation having a particle diameter of 1 μm to about 150 μm, and a formulation having a particle diameter less than 1 μm smaller than a microsphere is referred to as a nanosphere. For example, when a biologically active substance is incorporated in a synthetic or natural polymer, the biologically active substance can be continuously released locally, or the biologically active substance can be targeted to a tissue.

A sustained release microsphere formulation which gradually releases a biologically active substance at a constant rate, needs to be, for example, a formulation in which a biodegradable polymer, a biologically active substance, an additive, a solvent and the like are appropriately adjusted. In order for a sustained release microsphere formulation to effectively exhibit a pharmacological effect in vivo for a predetermined period of time, it is necessary to continuously release the biologically active substance in vivo for a predetermined period of time, by appropriately adjusting the initial release amount of the biologically active substance and its release rate during a subsequent release period.

One of the important factors for determining the release rate of the biologically active substance is a kind of biodegradable polymers. Particularly, the most widely used lactic acid-glycolic acid copolymer (polylactide-co-glycolide, PLGA) has a different biodegradation rate depending on its physicochemical properties such as a ratio of lactic acid and glycolic acid, its molecular weight, its affinity with water and the like, and thus, the biodegradation rate can be adjusted to a desired release period (Patent Literature 1).

A microsphere of PLGA can be produced using, for example, a method of drying in liquid, a spray drying method, a spray freeze drying method, a drying method using a supercritical fluid process, a double emulsification method, or the like. When a biologically active substance is lipophilic, the most common production method among these methods is a method of drying in liquid in which PLGA and the biologically active substance are dissolved or dispersed in an organic solvent, mixed and emulsified with an aqueous solution in which polyvinyl alcohol (PVA) is dissolved, and the solvent is removed from the emulsion.

Patent Literature 1 discloses a method of producing a sustained release microsphere containing a biodegradable polymer such as PLGA and a peptide medicine by a spray drying method, a spray freeze drying method or a drying method using a supercritical fluid process. However, Patent Literature 1 does not describe how much the particle diameter of the sustained release microsphere varies, and whether a uniformly dispersed microsphere is obtained.

Patent Literature 2 discloses a method of producing PLGA microparticles by a method of drying in liquid using a mixed solvent comprising a halogenated hydrocarbon and a water-immiscible organic solvent having a solubility of a medicine of 0.3% (W/V) or more. Patent Literature 2 describes that particle diameters (median diameters) of the microparticles obtained in Production Examples 1 and 2 are respectively 14 and 16 μm, but does not describe how much the particle diameter of the sustained release microsphere varies, and whether a uniformly dispersed microsphere is obtained.

Patent Literatures 3 to 5 disclose PLGA nanoparticles containing a biologically active substance. These nanoparticles are mainly intended for targeting to a specific tissue, and are nanoparticles of several tens nm to several hundreds nm which can pass through microscopic pores of blood capillaries. However, Patent Literatures 3 to 5 do not describe an approximately spherical microsphere of 1 μm or more much larger than these nanoparticles at all. Even with the technique of Patent Literatures 3 to 5, a person skilled in the art could not produce an approximately spherical microsphere having a particle diameter of 1 μm or more, which particle diameter distribution is sharp.

Patent Literature 6 discloses a formulation which releases leuprorelin acetate of a luteinizing hormone releasing hormone derivative, during from about 1 month to several months by subcutaneous injection. The formulation has a problem that a distribution of the particle diameters is very wide from 1 μm to 400 μm. Therefore, Patent Literature 7 proposes as a method for solving this problem, a method of producing a microsphere in which a biologically active substance is encapsulated in a polymer for a carrier by a double emulsification method. However, the leuprorelin acetate containing the microspheres obtained in Examples 1 to 5, have large variation in the particle diameters and unsharp particle diameter distribution, and are unsatisfactory, as explained below.

Patent Literature 8 discloses a method of producing an aqueous resin microparticle dispersion by precipitating in a thin film fluid formed in the space between the processing surfaces being capable of approaching to and separating from each other at least one of which rotates relative to the other. However, the particle diameters of the microparticles obtained in examples are 28 to 74 nm. The aqueous resin microparticle dispersion of Patent Literature 8 is used in the fields such as paints, inks and adhesives. Patent Literature 8 does not describe approximately spherical PLGA microparticles comprising a biologically active substance, having a particle diameter of 1 μm or more which is far bigger than these nanoparticles.

CITATION LIST

Patent Literature

Patent Literature 1: JP 2005-035994
Patent Literature 2: JP 2005-015476
Patent Literature 3: JP 4856752
Patent Literature 4: JP 2006-131577
Patent Literature 5: JP 2018-052922
Patent Literature 6: JP 2653255
Patent Literature 7: JP 2014-224114
Patent Literature 8: JP 2009-132871

SUMMARY OF THE INVENTION

Technical Problem

A PLGA microsphere having an average volume-based particle diameter of 1 μm or more and 150 μm or less which is not a nanosphere, cannot be put in practice as its release period is designed, unless the shape and the particle diameters are adjusted. For example, when the particle diameters are not adjusted and wide particle diameters are included, a large amount of the biologically active substance is released from the minute particles at the initial period after administration to generate the problem of the initial burst. Since particles coarser than those having the appropriate particle diameters induce aggregation, their removal is necessary. When dispersion in the microspheres is non-uniform, there is the problem of the initial burst. In addition, since injection formulations are the most suitable for sustained-release microspheres, the production steps are required to be shortened as much as possible from the viewpoint of ensuring sterility.

In view of the above problems, an object of the present invention is to provide approximately spherical PLGA microparticles having an average volume-based particle diameter of 1 μm or more and 150 μm or less wherein there are few coarse particles or ultrafine particles without a classification step, and the particle diameter distribution is sharp around the target particle diameter; and a method capable of efficiently producing the approximately spherical PLGA microparticles.

Solution to the Problem

The present inventors earnestly studied to solve the above problem. As a result of that, the present inventors have surprisingly found approximately spherical PLGA microparticles having uniform particle diameters which are produced for the first time by using a specific manufacturing apparatus; and a method capable of efficiently producing the approximately spherical PLGA microparticles. Namely, the present inventions are as follows.

[1] The first embodiment of the present invention is approximately spherical lactic acid-glycolic acid copolymer (PLGA) microparticles comprising a biologically active substance, wherein an average volume-based particle diameter of the PLGA microparticles is 1 μm or more and 150 μm or less, and a Reactive Span Factor (R.S.F.) of the PLGA microparticles is satisfied with formula (1):

$$0.1 < (R.S.F) \leq 1.7 \quad \text{formula (1)}$$

wherein an R.S.F. means (D90−D10)/D50,

D90 is a particle diameter (μm) corresponding to the cumulative 90% by volume of the cumulative particle diameter distribution from the small particle side, D50 is a particle diameter (μm) corresponding to the cumulative 50% by volume of the cumulative particle diameter distribution from the small particle side, and D10 is a particle diameter (μm) corresponding to the cumulative 10% by volume of the cumulative particle diameter distribution from the small particle side.

[2] The second embodiment of the present invention is the approximately spherical PLGA microparticles according to [1], wherein the biologically active substance is a lipophilic biologically active substance.

[3] The third embodiment of the present invention is a sustained release formulation comprising the approximately spherical PLGA microparticles according to [1] or [2].

[4] The fourth embodiment of the present invention is a method of producing the approximately spherical PLGA microparticles according to [1] or [2], using a processing apparatus in which microparticle forming is performed between the processing surfaces being capable of approaching to and separating from each other at least one of which rotates relative to the other.

[5] The fifth embodiment of the present invention is the method of producing the approximately spherical PLGA microparticles according to [4], wherein when microparticle forming is performed using the processing apparatus, the outlet of the processed fluid has a positive pressure over the atmospheric pressure.

[6] The six embodiment of the present invention is the method of producing the approximately spherical PLGA microparticles according to [4] or [5], wherein the surface pressure in a shut down period of the processing surfaces being capable of approaching to and separating from each other at least one of which rotates relative to the other in the processing apparatus is 20 g/cm$^2$ to 250 g/cm$^2$.

[7] The seventh embodiment of the present invention is the method of producing the approximately spherical PLGA microparticles according to any one of [4] to [6], which comprises a step of forming particles in which the approximately spherical PLGA microparticles are formed by continuously introducing into the processing apparatus, a PLGA solution obtained by dissolving or dispersing PLGA and the biologically active substance in a good solvent of PLGA and a solution containing a poor solvent of PLGA.

[8] The fourth embodiment of the present invention is the method of producing the approximately spherical PLGA microparticles according to [7], wherein the PLGA solution and the solution containing the poor solvent are respectively aseptically filtered, and then the approximately spherical PLGA microparticles are produced in an aseptic environment.

[9] The ninth embodiment of the present invention is the method of producing the approximately spherical PLGA microparticles according to any one of [4] to [8], wherein the biologically active substance is a lipophilic biologically active substance.

Advantageous Effects of the Invention

The approximately spherical PLGA microparticles of the present invention are approximately spherical PLGA microparticles comprising a biologically active substance, having an average volume-based particle diameter of 1 μm or more and 150 μm or less wherein the particle diameter distribution is sharp. The approximately spherical PLGA microparticles of the present invention can appropriately control the initial release amount of the biologically active substance and its release rate during a subsequent release period, and can continuously release the biologically active substance in vivo for a predetermined period of time, thereby pharmacological effects can be efficiently exhibited.

The method of producing the approximately spherical PLGA microparticles of the present invention, produces the approximately spherical PLGA microparticles using a processing apparatus in which microparticle forming is performed between the processing surfaces being capable of approaching to and separating from each other at least one of which rotates relative to the other. The method can efficiently produce the approximately spherical PLGA microparticles wherein there are few coarse particles or ultrafine particles without a classification step, and the particle diameter distribution is sharp around the target particle diameter.

In one aspect of the method of producing the approximately spherical PLGA microparticles of the present invention, when microparticle forming is performed using the processing apparatus, the outlet of the processed fluid has a positive pressure over the atmospheric pressure. The processing surfaces installed facing each other have a pressure distribution, and the pressure usually drops in the direction of discharge from the processing surfaces, and the pressure approaches the atmospheric pressure at the outlet of the processed fluid. By this method, the processed fluid can be stably discharged, in order to counteract the residual pressure generated at the outlet of the processing surfaces. When the residual pressure remains between the processing surfaces, the processed fluid may flush due to pressure fluctuations at the processed fluid discharge part, causing generation of microparticles. However, this method prevents such situations.

In one aspect of the method of producing the approximately spherical PLGA microparticles of the present invention, the surface pressure in a shut down period of the processing surfaces being capable of approaching to and separating from each other at least one of which rotates relative to the other in the processing apparatus is adjusted. Preferably, the surface pressure is 20 $g/cm^2$ to 250 $g/cm^2$. By this method, the particle diameters can be controlled. When the surface pressure is too low, the thin film is not stable and the particle diameter distribution becomes wide. When the surface pressure is too high, it becomes difficult to adjust the target particle diameter.

In one aspect of the method of producing the approximately spherical PLGA microparticles of the present invention, a step of forming particles is included in which the approximately spherical PLGA microparticles are formed by continuously introducing into the processing apparatus, a PLGA solution obtained by dissolving or dispersing PLGA and the biologically active substance in a good solvent of PLGA and a solution containing a poor solvent of PLGA. After the PLGA solution and the solution containing the poor solvent are respectively aseptically filtered, approximately spherical PLGA microparticles can be produced in an aseptic environment.

BRIEF DESCRIPTION OF THE DRAWINGS

FIG. 1 shows a schematic half sectional view of a microparticle forming processing apparatus used for the method of producing the approximately spherical PLGA microparticles of the present invention.

DESCRIPTION OF THE INVENTION

1. Approximately Spherical PLGA Microparticles

<PLGA>

Figure 2:
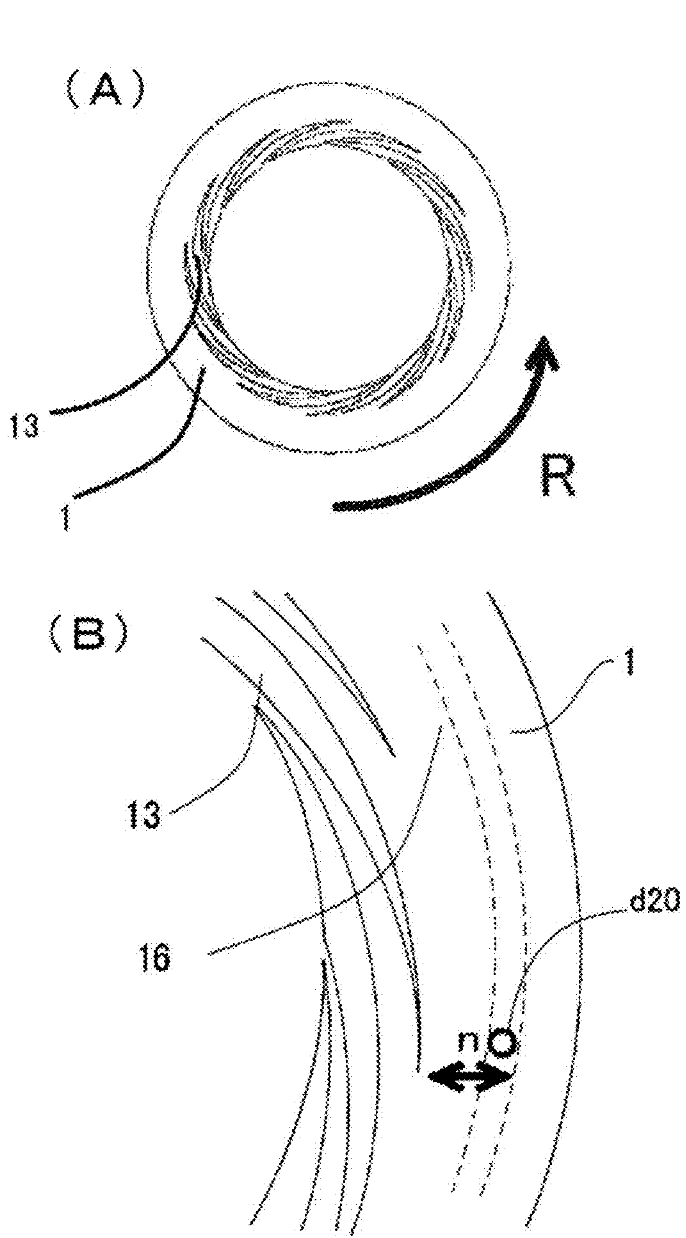
FIG. 2 shows (A) a schematic plan view of the first processing surface of the microparticle forming processing apparatus of FIG. 1, and (B) an enlarged view of a main part of the first processing surface.

PLGA is a lactic acid-glycolic acid copolymer having a constitutional unit derived from lactic acid and a constitutional unit derived from glycolic acid. PLGA may comprise another biodegradable polymer such as polylactide (PLA), polyglycolide (PGA) and the like. The PLGA described herein is described as an example, and the present invention is not limited to the described PLGA.

The molar ratio (L:G) of the constitutional unit (L) derived from lactic acid and the constitutional unit (G) derived from glycolic acid in PLGA is not particularly limited, and may be appropriately selected according to the intended purpose. A preferable molar ratio (L:G) is 1:99 to 99:1, more preferably 25:75 to 99:1, further preferably 30:70 to 90:10, particularly preferably 50:50 to 85:15.

PLGA used in the approximately spherical PLGA microparticles of the present invention can be produced, for example, by heating and condensation polymerization of lactic acid and glycolic acid under a weakly reduced pressure using an ion exchange resin as a catalyst. In this case, lactide may be used in place of lactic acid. PLGA may be a commercially available product. A commercially available product may be purchased from, for example, FUJIFILM Wako Pure Chemical Corporation, Taki Chemical Co., Ltd., Evonic Rohm GmbH, Merck KGaA, Sigma-Aldrich Co., LLC, and the like.

The content of PLGA in the approximately spherical PLGA microparticles of the present invention is not particularly limited, and may be appropriately selected according to the intended purpose. The content is preferably 1% by mass or more, more preferably 30% by mass or more and 95% by mass or less, and particularly preferably 50% by mass or more and 90% by mass or less.

<PLGA Microparticles>

The approximately spherical PLGA microparticles of the present invention include PLGA and a biologically active substance. The approximately spherical PLGA microparticles may further contain a dispersing agent and another component, if necessary. The biologically active substance, dispersing agent, another component and the like are dispersed in the approximately spherical PLGA microparticles.

[Biologically Active Substance]

A biologically active substance contained in the approximately spherical PLGA microparticles of the present invention is not particularly limited, and may be appropriately selected according to the intended purpose. The biologically active substance may be, for example, a pharmaceutical compound, a functional food compound, a functional cosmetic compound, and the like. Approximately spherical PLGA microparticles microsphere containing a pharmaceutical compound can be suitably used, for example, as a sustained release pharmaceutical formulation. The biologically active substance includes both a lipophilic biologically active substance and a hydrophilic biologically active substance. A preferable biologically active substance is a lipophilic biologically active substance. A lipophilic biologically active substance means, for example, a substance having a log P value of water/octanol distribution coefficient of 3 or more, and a biologically active substance not contained in a lipophilic biologically active substance is classified as a hydrophilic biologically active substance. The water/octanol distribution coefficient can be measured according to the Japanese Industrial Standard: JIS Z 7260-107 (2000): Flask shaking method. The biologically active substance is not particularly limited as long as a sustained release formulation comprising the biologically active substance is desired, and may be appropriately selected according to the intended purpose. The biologically active substance includes any form of a salt, hydrate, and the like.

[Dispersing Agent]

A dispersing agent may be used for dispersing the biologically active substance. The dispersing agent may be a low molecular weight dispersing agent or a high molecular weight polymer dispersing agent. A low molecular weight dispersing agent means a compound having a mass average molecular weight of less than 15,000. A high molecular weight polymer dispersing agent means a compound having a mass average molecular weight of 15,000 or more, including repeated covalent bonds between one or more of monomers.

The low molecular weight dispersing agent is not particularly limited as long as it is acceptable for a pharmaceutical compound, a functional food compound, a functional cosmetic compound, and the like, and may be appropriately selected according to the intended purpose. A specific example thereof includes a lipid, a saccharide, a cyclodextrin, an amino acid, an organic acid, another component, and the like. These may be used alone or in combination of two kinds or more thereof.

The lipid is not particularly limited, and may be appropriately selected according to the intended purpose. The lipid may be, for example, a medium chain or long chain monoglyceride, diglyceride or triglyceride, a phospholipid, a vegetable oil (e.g. soybean oil, avocado oil, squalene oil, sesame oil, olive oil, corn oil, rape-seed oil, safflower oil, sunflower oil, etc.), a fish oil, a flavoring oil, a water-insoluble vitamin, a fatty acid, and a mixture thereof, a derivative thereof and the like. These may be used alone or in combination of two kinds or more thereof.

The sugar is not particularly limited, and may be appropriately selected according to the intended purpose. The sugar includes, for example, glucose, mannose, idose, galactose, fucose, ribose, xylose, lactose, sucrose, maltose, trehalose, turanose, raffinose, maltotriose, acarbose, water-soluble cellulose, synthetic cellulose, sugar alcohol, glycerin, sorbitol, lactitol, maltitol, mannitol, xylitol, erythritol, polyol, and a derivative thereof, and the like. These may be used alone or in combination of two kinds or more thereof.

The another component is not particularly limited and may be appropriately selected according to the intended purpose. The another component is preferably one which can be used for a medicine so far.

<Properties of Approximately Spherical PLGA Microparticles>

[Average Volume-Based Particle Diameter]

The average volume-based particle diameter of the approximately spherical PLGA microparticles of the present invention is 1 μm or more and 150 μm or less, preferably 10 μm or more and 100 μm or less, and more preferably 20 μm or more and 75 μm or less. The average volume-based particle diameter may be measured using a laser diffraction particle diameter distribution measuring apparatus. In the present invention, when the average volume-based particle diameter exceeds 150 μm, the problem of an initial burst occurs due to non-uniform dispersibility of the biologically active substance in the PLGA microparticles, which tends to cause aggregation and sedimentation, and to lead to difficult processing in subsequent steps. When the average volume-based particle diameter is smaller than 1 μm, the problem of an initial burst occurs remarkably.

[Reactive Span Factor (R.S.F.)]

A Reactive Span Factor (R.S.F.) of the PLGA microparticles of the present invention is satisfied with formula (1):

$$0.1 < (R.S.F) \leq 1.7 \quad \text{formula (1)}$$

wherein an R.S.F. means (D90–D10)/D50,

D90 is a particle diameter (μm) corresponding to the cumulative 90% by volume of the cumulative particle diameter distribution from the small particle side, D50 is a particle diameter (μm) corresponding to the cumulative 50% by volume of the cumulative particle diameter distribution from the small particle side, and D10 is a particle diameter (μm) corresponding to the cumulative 10% by volume of the cumulative particle diameter distribution from the small particle side.

The particle diameter measurement results of the leuprolide acetate containing microspheres obtained in Examples 1 to 5 of Patent Literature 7 are shown in Table 3 of Patent Literature 7. The particle diameter distributions (D10, D50 and D90) and the average particle diameters are as shown in Table 1 below. As shown in Table 1, R.S.F. are obtained from these numerical values and are 2.17 to 9.10, which greatly exceed the range of the formula (1) in the present invention. As described above, the microspheres of Patent Literature 7 have large variation in the particle diameters and unsharp particle diameter distribution, and are unsatisfactory.

TABLE 1

| | Particle diameter distribution [μm] | | | Average particle diameter | |
|---|---|---|---|---|---|
| | D10 | D50 | D90 | [μm] | R.S.F. |
| Example 1 | 1.6 | 3.8 | 16.5 | 7.46 | 3.92 |
| Example 2 | 1.4 | 5.1 | 47.8 | 15.0 | 9.10 |
| Example 3 | 3.7 | 24.7 | 79.7 | 34.9 | 3.08 |
| Example 4 | 8.1 | 31.3 | 76.0 | 42.9 | 2.17 |
| Example 5 | 4.8 | 20.8 | 61.3 | 28.2 | 2.72 |

R.S.F. can be measured using a laser diffraction type particle size distribution measuring device (SALD-7000, Shimadzu Corporation, or Microtrac MT-3300, MicrotracBEL Corporation). When R.S.F. is larger than 1.7, the particle diameter distribution cannot be said to be sharp. Since a classification step is required for approximately spherical microparticles having such R.S.F., the yield of the approximately spherical microparticles decreases.

The approximately spherical PLGA microparticles of the present invention preferably have a coefficient of variation (CV value) of 60% or less, more preferably 50% or less, still more preferably 40% or less, even more preferably 30% or less, particularly preferably 20% or less, and particularly even more preferably 10% or less. Here, the CV value is calculated by "standard deviation of volume-based particle diameters"/"average volume-based particle diameter" in particle diameter distribution measurement.

The approximately spherical PLGA microparticles of the present invention can appropriately control the initial release amount of a biologically active substance and its release rate during a subsequent release period, and can continuously release the biologically active substance in vivo for a predetermined period of time.

2. Sustained Release Formulation

By using the approximately spherical PLGA microparticles of the present invention, a sustained release formulation containing the approximately spherical PLGA microparticles can be prepared. The sustained release formulation of the present invention can appropriately control the initial release amount of a biologically active substance and its release rate during a subsequent release period, and can continuously release the biologically active substance in vivo for a predetermined period of time, and a pharmacological effect can be effectively exhibited.

The sustained release formulation of the present invention can be simply administered as an injection, an implant or a transdermal formulation, directly to a lesion such as a muscle, subcutaneous tissue, blood vessel, organ, joint cavity, tumor, or the like. It may be administered as various other formulations. For example, when preparing the sustained-release preparation of the present invention as an injection formulation, the sustained release injection formulation as an aqueous suspension may be prepared together with a dispersing agent (Tween 80, HCO 60, carboxy methylcellulose, sodium alginate, etc.), a preservative (methylparaben, propylparaben, etc.), an isotonizing agent (sodium chloride, mannitol, sorbitol, glucose, etc.) and the like. Alternatively, the sustained release injection formulation as an oil suspension may be prepared with a vegetable oil such as soybean oil, sesame oil, corn oil, and the like.

3. Method of Producing Approximately Spherical PLGA Microparticles

<Microparticle Forming Processing Apparatus>

Figure 1:
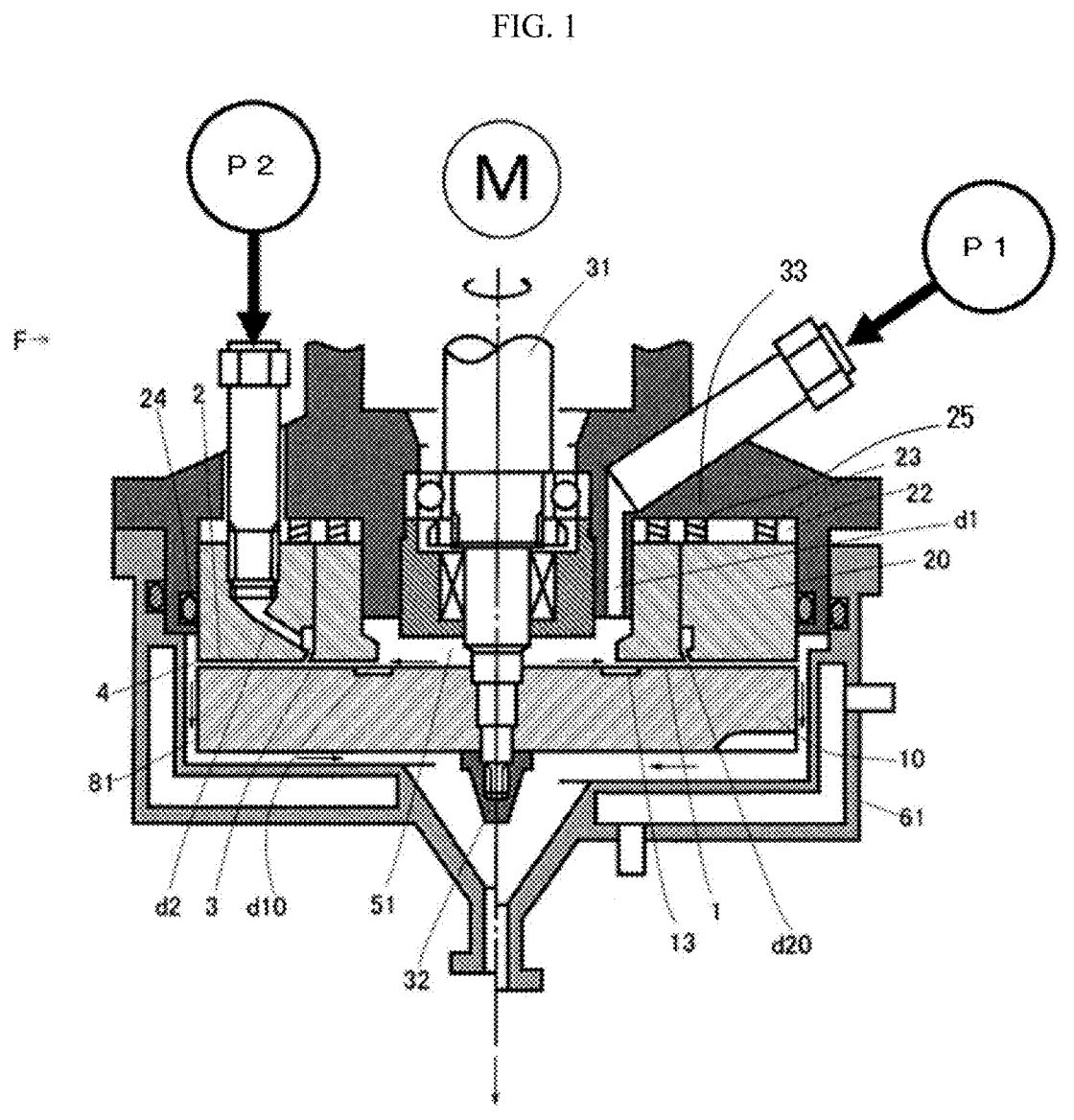

A microparticle forming processing apparatus which can be used in the method of producing the approximately spherical PLGA microparticles of the present invention (hereinafter referred to as a fluid processing apparatus, or simply a processing apparatus) is explained below in reference to FIG. 1 to FIG. 3.

The microparticle forming processing apparatus is a processing apparatus in which microparticle forming is performed between the processing surfaces being capable of approaching to and separating from each other at least one of which rotates relative to the other. As the microparticle forming processing apparatus, the similar processing apparatus to that described in Patent Literature 8 is preferably used. Specifically, the processing apparatus is an apparatus in which the fluids to be processed are processed in the processing space defined by at least two processing surfaces rotating relative to each other. The processing apparatus is an apparatus in which the first fluid being the first fluid to be processed among the fluids to be processed is introduced into the processing space; and the second fluid being the second fluid to be processed among the fluids to be processed is introduced into the processing space from a different flow path which is independent of the flow path introducing the first fluid and has an opening leading to the processing space; and the first fluid and the second fluid are mixed in the processing space, and the processing of fluids are continuously performed. In other words, the processing apparatus is an apparatus in which the above respective fluids are merged into a thin film fluid in a processing space defined by a disk-shaped processing surface facing the axial direction of rotation; and the above fluids to be processed are processed in the thin film fluid; and the processed fluids are discharged from the processing space. Although this apparatus is the most suitable for processing a plurality of fluids to be processed, this apparatus can also be used for processing a single fluid to be processed in the processing space.

In FIG. 1, the top and bottom of the figure correspond to the top and bottom of the apparatus, but in the present invention, the top, bottom, front, back, left and right only show a relative positional relationship, and do not specify an absolute position. In FIG. 2(A) and FIG. 3(B), R indicates a rotation direction. In FIG. 3(B), C indicates a centrifugal force direction (radial direction). In the present application, a column should not be interpreted as a mathematical column, but a column includes a column, a hollow cylinder (hereinafter referred to as a column), and a cylinder having a top.

It is important for deepening understanding of the present invention, to explain the structure, operation, etc. of the microparticle forming processing apparatus used in the present invention which is common to the apparatus described in Patent Literature 8. Accordingly, the matters in relation to the processing space are explained at first.

[Processing Surfaces]

This microparticle forming processing apparatus includes two opposing first and second processing parts 10 and 20, and at least one of the processing parts rotates with respect to the other processing part. The facing surfaces of both the processing parts 10 and 20 are respectively the processing surfaces. The first processing part 10 includes the first processing surface 1, and the second processing part 20 includes the second processing surface 2.

Both the processing surfaces 1 and 2 define the processing space 3. In the processing space 3, processing of fluids such as mixing the fluids to be processed are performed. The processing space 3 is an annular space, as described later.

The distance between both the processing surfaces 1 and 2 can be appropriately changed, but in this embodiment, it is usually adjusted to a minute distance of 1 mm or less, for example, about 0.1 μm to 150 μm. As a result, the fluid to be processed passing between both the processing surfaces 1 and 2 becomes a forced thin film fluid forced by both the processing surfaces 1 and 2.

When a plurality of fluids to be processed including the first fluid and the second fluid are processed by using this microparticle forming processing apparatus, the microparticle forming processing apparatus is connected to the flow path of the first fluid, which is introduced from the upstream end (inside the annular space in this example) of the processing space 3 defined by both the processing surfaces 1 and 2. At the same time, the processing space 3 forms a part of the flow path of the second fluid, which is different from the flow path of the first fluid. Then, in the processing space 3 between both the processing surfaces 1 and 2, processing of fluids is performed, such as mixing and emulsifying both the fluids to be processed of the first fluid and the second fluid.

Specifically, the microparticle forming processing apparatus includes the second holder 22 that holds the second processing part 20, the contact surface pressure applying mechanism, the rotation drive mechanism M, the first introduction part d1, the second introduction part d2, and the fluid pressure applying mechanisms P1 and P2.

In this embodiment, the second processing part 20 is arranged above the first processing part 10. The lower surface of the second processing part 20 is the second processing surface 2, and the upper surface of the first processing part 10 is the first processing surface 1.

As shown in FIG. 1, in this embodiment, the first processing part 10 is a disk body having no central opening. The second processing part 20 is an annular body, and more specifically, a ring-shaped disc. In this embodiment, since the first processing surface 1 is disk-shaped and the second processing surface 2 is annular, the processing space 3 defined between both the two processing surfaces 1 and 2 constitutes an annular space, that is, an annular flow path. The second processing part 20 may have a disk shape without an opening in the center, provided that the fluids to be processed containing the first fluid and the second fluid can be introduced.

The first and second processing part 10 and 20 can be formed of a single material or a combination of a plurality of materials. The material thereof may be a metal, ceramics such as silicon carbide (SiC), or a sintered metal, abrasion resistant steel, sapphire, other metals that have been hardened, hard materials that have been lined, coated, or plated. In this embodiment, at least a part of the first and second processing surfaces 1 and 2 is mirror-polished.

[Rotation of Processing Part]

At least one processing part of the first processing part 10 and the second processing part 20 rotates relative to the other processing part by the rotation drive mechanism M such as an electric motor. The drive shaft of the rotation drive mechanism M is connected to the rotation shaft 31. In this example, the first processing part 10 attached to the rotation shaft 31 rotates with respect to the second processing part 20. In the present embodiment, the rotation shaft 31 is fixed to the center of the first processing part 10 with the fixture 32 such as a screw, and its rear end is connected to the drive shaft of the rotation drive mechanism M. The driving force of the rotation drive mechanism M is transmitted to the first processing part 10 to rotate the first processing part 10. The support part 33 for axially supporting the rotation shaft 31 is provided at the center of the annular shape of the annular second holder 22. Of course, the second processing part 20 held by the second holder 22 may rotate, or both may rotate.

[Approaching and Separating of Processing Surfaces]

In this embodiment, at least one of the first processing part 10 and the second processing part 20 can approach to and separate from at least one of the other in the axial direction of the rotation shaft 31. Both the processing surfaces 1 and 2 can approach to and separate from each other.

In this embodiment, the first processing part 10 is configured to be fixed in the axial direction and to rotate in the circumferential direction. The second processing part 20 approaches to and separates from the first processing part 10 in the axial direction, and the second processing part 20 is retractably housed in the accommodating part 23 provided in the second holder 22, using a sealing mechanism such as the O-ring 24. The accommodating part 23 is a recess of the second processing part 20 for accommodating its portion mainly axially opposite to the side of the second processing surface 2, and is a groove exhibiting a circle in a plan view, namely, is formed in an annular shape.

The second processing part 20 may be arranged in the accommodating part 23 of the second holder 22 so that it can only be moved in parallel in the axial direction. It can also be accommodated in a state where the clearance is increased. The second processing part 20 may be held by a floating mechanism that holds the second processing part 20 in a three-dimensionally displaceable manner.

[Fluid Pressure Applying Mechanism]

The fluids to be processed (the first fluid and the second fluid in this example) are supplied to the microparticle forming processing apparatus by the fluid pressure applying mechanisms P1 and P2. Various pumps may be used for the fluid pressure applying mechanisms P1 and P2, and the fluids to be processed may be supplied to the microparticle forming processing apparatus at a predetermined pressure. Further, in order to suppress occurrence of pulsation during pumping, a pressure applying apparatus provided with a pressure container may be adopted as the fluid pressure applying mechanisms P1 and P2. The fluid to be processed may be pumped by introducing a pressurizing gas into a pressure container containing the fluid to be processed and pushing out the fluid to be processed by the pressure.

[Movement of Fluid to be Processed]

Pressure is applied to the above fluids to be processed by the fluid pressure applying mechanisms P1 and P2. Under this pressurized condition, the fluids to be processed containing the first fluid and the second fluid are introduced into the space between both the processing surfaces 1 and 2 from the first introduction part d1 and the second introduction part d2.

In this embodiment, the first introduction part d1 is a flow path provided in the annular second holder 22, and one end thereof is connected to the tubular introduction space 51. The introduction space 51 is a cylindrical space defined by the lower surface of the support part 33, the lower surface on the inner peripheral side of the second holder 22, the inner peripheral surface of the second processing part 20 and the first processing surface 1.

The second introduction part d2 is a flow path provided inside the second processing part 20, and one end thereof is open to the second processing surface 2. This opening is a direct introduction opening to the processing space 3 (the second introduction opening d20).

The first fluid is introduced from the first introduction part d1 into the processing space 3 through the introduction space 51 from the upstream end of the processing space 3 which is a gap on the inner diameter side between both the processing parts 10 and 20. This gap becomes the first introduction opening d10. The first fluid introduced from the first introduction opening d10 into the processing space 3 becomes a thin film fluid between the first processing surface 1 and the second processing surface 2, and passes outside both the processing parts 10 and 20. The second fluid pressurized at a predetermined pressure is supplied from the second introduction opening d20 of the second introduction part d2 between these processing surfaces 1 and 2, and merges with the first fluid which is a thin film fluid, and a reaction processing is carried out while or after mixing mainly by molecular diffusion. Only mixing mainly by molecular diffusion may be performed as these processing. These reaction processing may or may not be accompanied by crystallizing, crystallization, precipitation and the like.

The thin film fluid formed by the first fluid and the second fluid is discharged from both the processing surfaces 1 and 2 outside both the processing parts 10 and 20 after a microparticle forming processing. The fluid discharged from both the processing surfaces 1 and 2 outside both the processing parts 10 and 20 is received by the outer casing 61 arranged outside the first processing part 10. The fluid subjected to the microparticle forming processing is discharged to outside system (outside the apparatus). The fluid discharged from both the processing surfaces 1 and 2 outside both the processing parts 10 and 20 is released from the forcing by both the processing surfaces 1 and 2 and is discharged into the wider flow path space 81.

Since the first processing part 10 is rotating, the fluid to be processed in the processing space 3 does not move linearly from the inside to the outside, but moves in a substantially spiral shape from the inside to the outside, by acting the composite vector of the moving vector in the annular radial direction and the moving vector in the circumferential direction on the fluid to be processed.

In the motion of the fluid, a dimensionless number representing the ratio of the inertial force and the viscous force is called a Reynolds number, and is expressed by the following equation (2):

$$\text{Reynolds number Re} = \text{inertial force}/\rho VL/\mu = VL/\nu \qquad \text{Equation (2)}$$

wherein, ν (=μ/ρ) represents a kinematic viscosity, V represents a representative velocity, and L represents a representative length, ρ represents a density, and μ represents a viscosity.

The flow of the fluid is bounded by the critical Reynolds number. The flow becomes a laminar flow below the critical Reynolds number, and becomes a turbulent flow above the critical Reynolds number.

The space between both the processing surfaces 1 and 2 of the microparticle forming processing apparatus is adjusted to a minute interval of usually 1 mm or less, for example, about 0.1 μm to 150 μm. Thus, the amount of the fluid held between both the processing surfaces 1 and 2 is extremely small, the representative length L becomes very small, the centrifugal force of the thin film fluid passing between both the processing surfaces 1 and 2 becomes small, and the influence of the viscous force becomes large in the thin film fluid. Therefore, the Reynolds number becomes small, and the thin film fluid becomes a laminar flow.

Centrifugal force is a kind of inertial force in rotational motion, and is a force in the direction from the center to the outside. The centrifugal force F is represented by the following equation (3):

$$\text{Centrifugal force } F = ma = mv^2/R \qquad \text{Equation (3)}$$

wherein, a represents an acceleration, m represents a mass, v represents a velocity, and R represents a radius.

As described above, the amount of the fluid held between both the processing surfaces 1 and 2 is small. Thus, the ratio of the velocity to the mass of the fluid becomes very large, and the mass becomes negligible. Therefore, the influence of gravity can be ignored in the thin film fluid formed between both the processing surfaces 1 and 2.

[Balance of Forces]

Next, explained is the contact surface pressure applying mechanism for applying to the processing parts a force acting in a direction in which the first processing surface 1 and the second processing surface 2 approach to each other. In this embodiment, the contact surface pressure applying mechanism is provided on the second holder 22 and urges the second processing part 20 toward the first processing part 10. The contact surface pressure applying mechanism is a mechanism for generating a force (hereinafter referred to as a contact surface pressure) which applies to the first processing surface 1 of the first processing part 10 and the second processing surface 2 of the second processing part 20 in a direction of approaching to each other. Due to the balance between this contact surface pressure and the force of separating both the processing surfaces 1 and 2 such as the fluid pressures by the fluid pressure applying mechanisms P1 and P2, a thin film fluid having a minute film thickness of 1 mm or less in nm units or pm units. In other words, the balance of the forces keeps the distance between both the processing surfaces 1 and 2 at a predetermined minute distance.

In the embodiment shown in FIG. 1, the contact surface pressure applying mechanism is coordinated between the accommodating part 23 and the second processing part 20. Specifically, the contact surface pressure applying mechanism is composed of the spring 25 urging the second processing part 20 in a direction of approaching the first processing part 10 and an urging fluid introduction part introducing an urging fluid such as air and an oil (not shown in the figure). The contact surface pressure is applied by the spring 25 and the fluid pressure of the urging fluid. The spring 25 and the fluid pressure of the urging fluid may be another force such as magnetic force or gravity, as far as the contact surface pressure is applied by any one of them.

The separation force generated by the pressure, viscosity or the like of the fluid to be processed pressurized by the fluid pressure applying mechanisms P1 and P2 against the urging of the contact surface pressure applying mechanism, moves the second processing part 20 from the processing part 10 and opens a minute interval between both the processing surfaces 1 and 2. In this way, due to the balance between the contact surface pressure and the separation force, the first processing surface 1 and the second processing surface 2 are set with an accuracy of μm, and the minute interval is set between both the processing surfaces 1 and 2. The above separation force may be one generated by the fluid pressure or viscosity of the fluid to be processed, the centrifugal force by the rotation of the processing part, the negative pressure applied to the urging fluid introduction part, and the force of the spring when the spring 25 is used as a tension spring, and the like. This contact surface pressure applying mechanism may be provided not in the second processing part 20, but in the first processing part 10, or may be provided in both.

[Recess and Micropump Effect]

Figure 3:
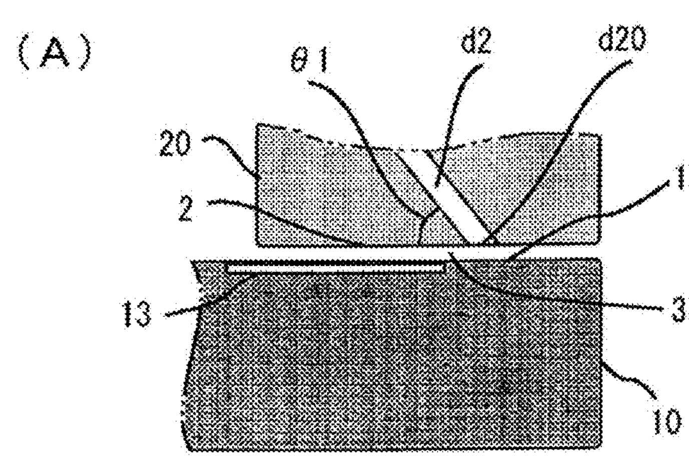
FIG. 3 shows (A) a sectional view of the second introduction part of the microparticle forming processing apparatus of FIG. 1, and (B) an enlarged view of a main part of the first processing surface for explaining the second introduction part.
Figure 3:
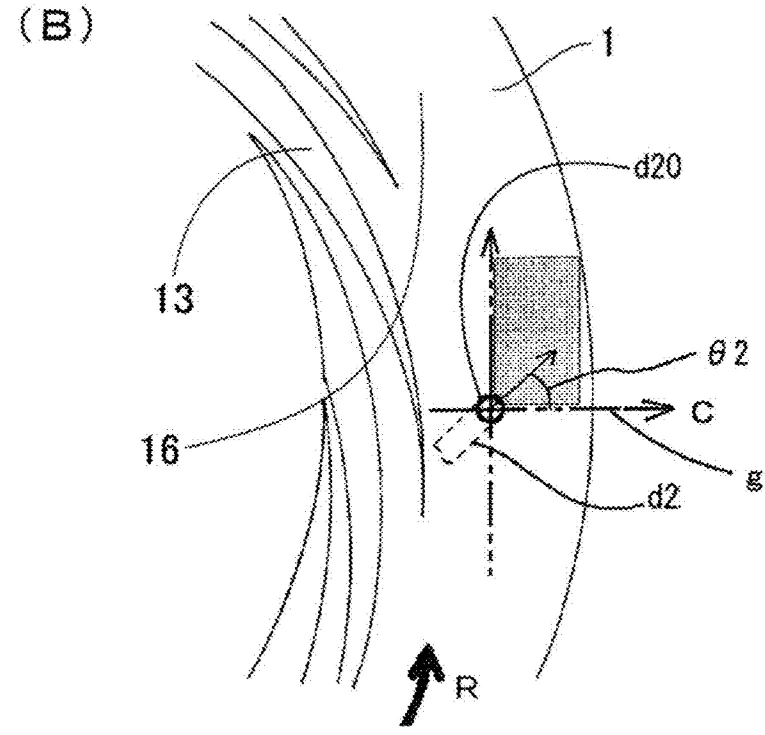
Figure 4:
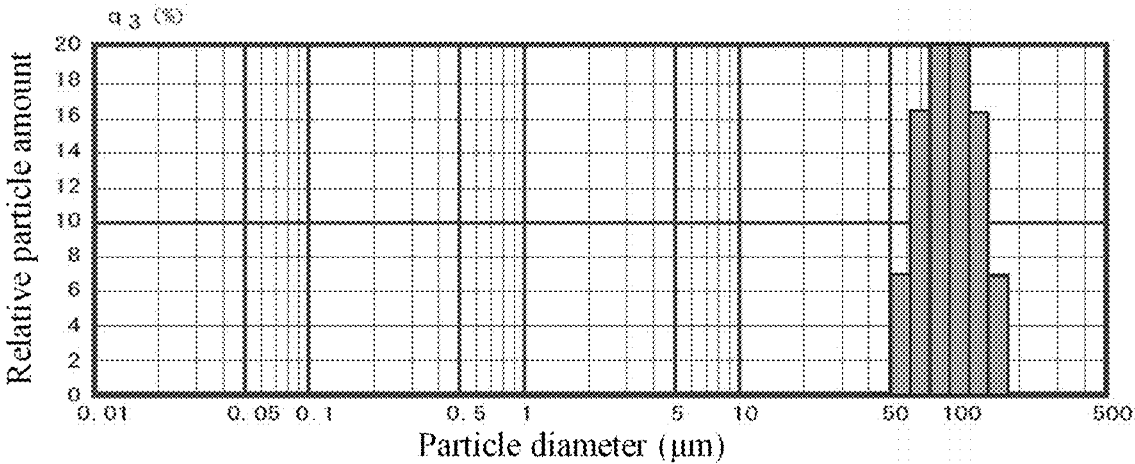
FIG. 4 shows a particle diameter distribution measurement result of Example 4.
Figure 5:
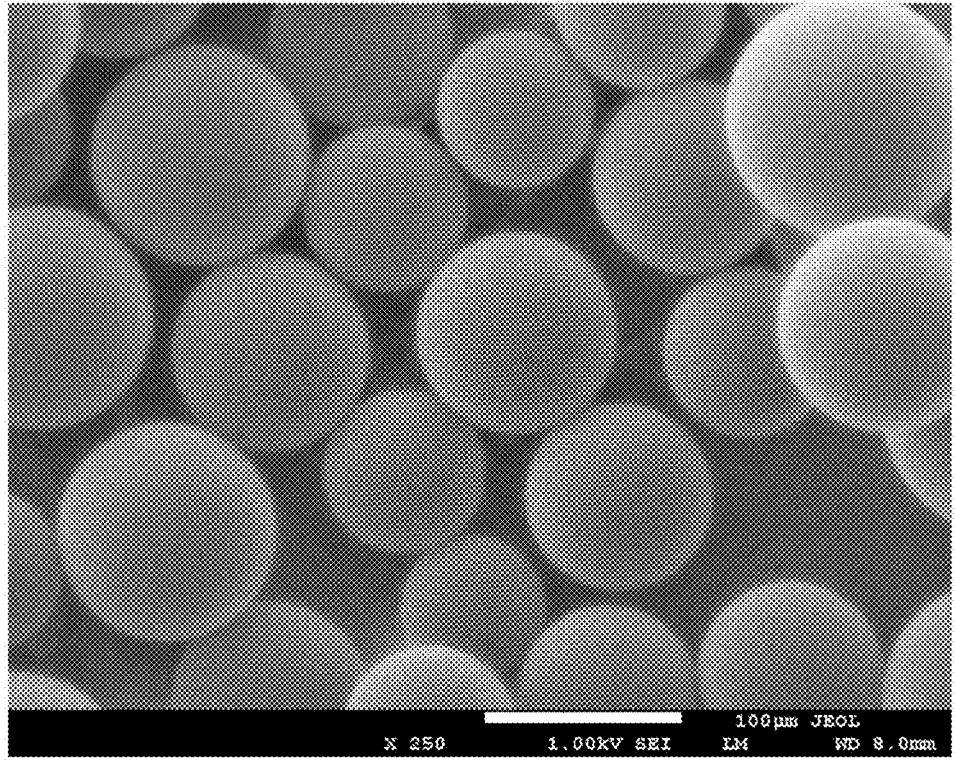
FIG. 5 shows an SEM observation result of Example 4.
Figures 6, 7:
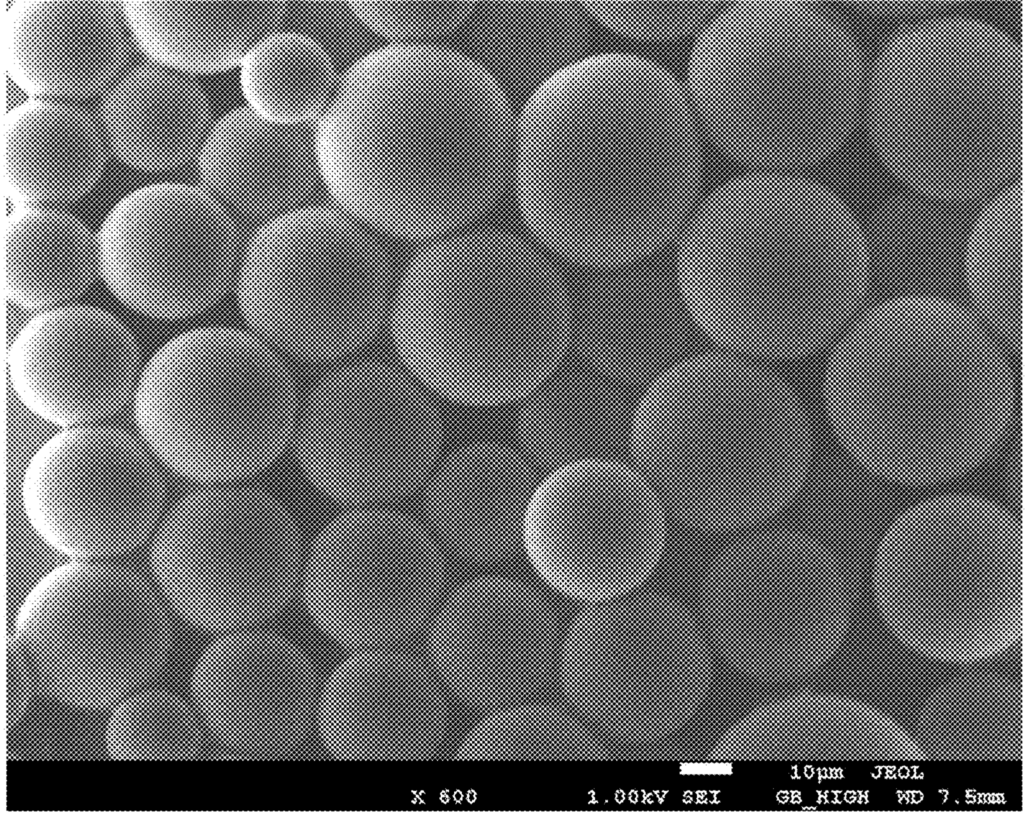
FIG. 6 shows a particle diameter distribution measurement result of Example 5.
FIG. 7 shows an SEM observation result of Example 5.
Figure 8:
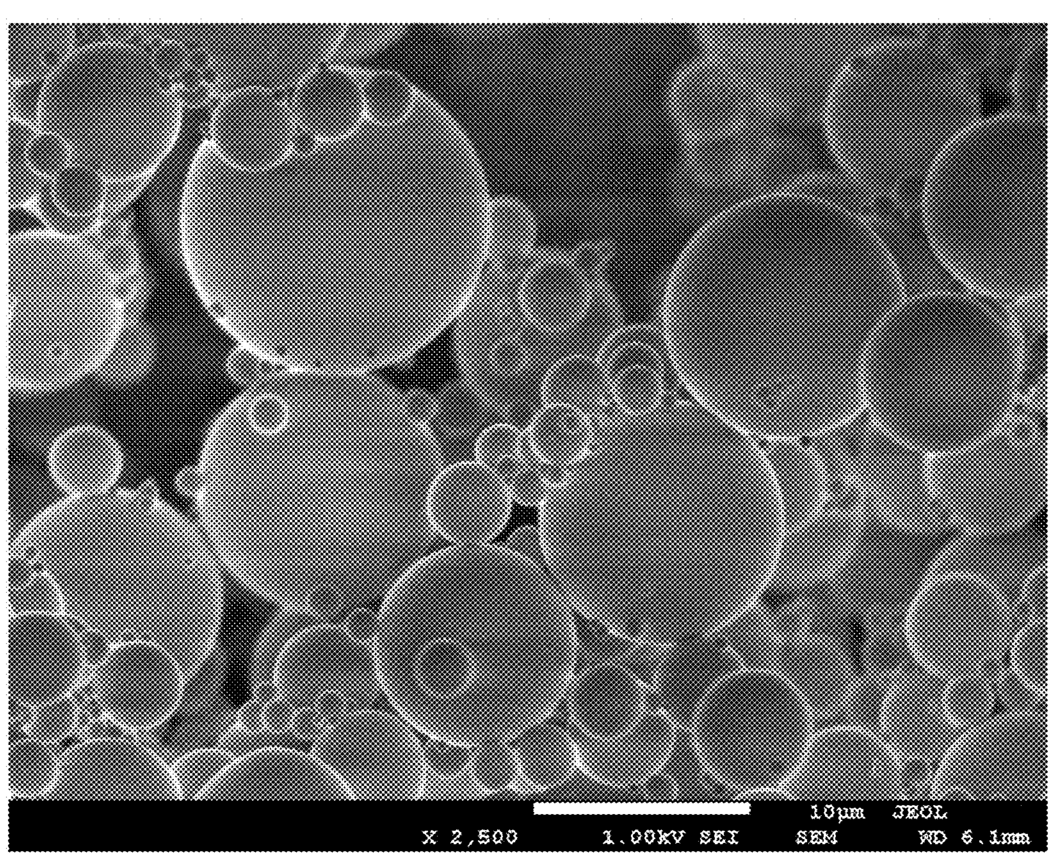
FIG. 8 shows an SEM observation result of Comparative Example 5.

As shown in FIG. 2, the groove-shaped recess 13 may be formed on the first processing surface 1 of the first processing part 10, extending from the center side of the first processing part 10 to the outside, that is, in the radial direction. As shown in FIG. 2(B), the planar shape of the recess 13 may be a shape that curves or extends in a spiral shape on the first processing surface 1, a shape that extends straight outward, though it is not shown in the figure, a shape that is bent or curved in a L character shape, a shape that is continuous, intermittent or branched, or the like. Further, the recess 13 may be formed on the second processing surface 2, or may be formed on both the first and second processing surfaces 1 and 2. Formation of such the recess 13 can give a micropump effect, and an effect that the fluids to be processed can be sucked between the first and second processing surfaces 1 and 2.

When the recess 13 is provided on the first processing surface 1, it is desirable that the end of the recess 13 reaches the introduction space 51. The tip of the recess 13 extends toward the outer peripheral surface side of the first processing part 10. The depth (cross-sectional area) thereof may be gradually decreased from the end toward the tip. The flat surface 16 without the recess 13 is provided between the tip of the recess 13 and the outer peripheral surface 11 of the first processing part 10.

[Rotation Speed and Fluid Processing]

When the second introduction opening d20 of the second introduction part d2 is provided on the second processing surface 2, the second introduction opening d20 is preferably provided at a position facing the flat surface 16 of the opposite first processing surface 1.

It is desirable that the second introduction opening d20 is provided on the downstream side (outside in this example) of the recess 13 of the first processing surface 1. In particular, it is desirable that the second introduction opening d20 is provided at a position facing the flat surface 16 which is more outer position from the position where the flow direction of the first fluid introduced into the processing space 3 is converted into the flow direction of the laminar flow in a spiral shape formed between the processing surfaces 1 and 2 by the micropump effect. Specifically, it is preferable that in FIG. 2B, the distance n in the radial direction from the outermost position of the recess 13 provided on the first processing surface 1 is about 0.5 mm or more. In particular, it is desirable that when microparticles are precipitated from the fluid, a plurality of fluids to be processed are mixed by molecular diffusion under a laminar flow condition, and the microparticle forming and precipitation are performed.

In order to process the fluids to be processed under the laminar flow condition in this way, the peripheral speed on the outer circumference of the first processing part 10 is appropriately 0.3 to 35 m/sec.

[Second Introduction Part]

The shape of the second introduction opening d20 may be a continuous opening, such as a concentric circular ring shape surrounding the central opening of the second processing surface 2 which is a ring-shaped disk, as shown in FIG. 1. It may be an independent opening such as a circle, as shown in FIG. 2(B) and FIG. 3(B). Further, when the second introduction opening d20 has a ring shape, the ring-shaped opening may be continuous over the entire circumference or may be partially discontinuous.

In the case where the ring-shaped second introduction opening d20 is provided concentrically around the central opening of the second processing surface 2, the processing may be performed under the same conditions in the circumferential direction when the second fluid is introduced into the processing space 3. Therefore, when it is desired to mass-produce a target product, it is preferable that the shape of the opening is a concentric annular shape.

The second introduction part d2 can have a directionality. For example, the introduction direction of the second processing surface 2 from the second introduction opening d20 is inclined at a predetermined elevation angle (θ1) with respect to the second processing surface 2, as shown in FIG. 3(A). This elevation angle (θ1) is set to more than 0 degree and less than 90 degree, and it is preferably set to 1 degree or more and 45 degree or less, in the case of a reaction having a faster reaction speed.

Further, it may have a directionality in a plane along the second processing surface 2, when the second introduction opening d20 is an independent opening hole, as shown in FIG. 3(B). The introduction direction of the second fluid is the outward direction away from the center in the radial component of the processing surfaces, and is the forward direction in the component with respect to the rotation direction of the fluid between the relatively rotating processing surfaces. In other words, it has a predetermined angle (θ2) from the reference line g to the rotation direction R, wherein the reference line g is the line segment in the radial direction passing through the second introduction opening d20 and in the outward direction. This angle (θ2) is also preferably set to more than 0 degree and less than 90 degree.

[Number of Types of Fluids to be Processed and Flow Paths]

Number of the types of fluids to be processed and flow paths thereof are two in the example of FIG. 1, but may be one or be three or more. In the example of FIG. 1, the second fluid is introduced into the processing space 3 from the second introduction part d2, but this introduction part may be provided in the first processing part 10 or both. Further, a plurality of introduction parts may be prepared for one type of fluid to be processed. In addition, the shape, size, and number of the respective introduction parts are not particularly limited and may be appropriately changed. Further, an introduction parts may be provided immediately before or further upstream of the first and second processing surfaces 1 and 2. Further, the expressions of the first and the second in respective fluids have only a meaning for identification that they are the nth of a plurality of existing fluids, and there may be also the third or higher fluids. Respective flow paths are hermetically sealed, and is liquid-tight (when the fluid to be processed is a liquid) and airtight (when the fluid to be processed is a gas).

When microparticle forming is performed using the microparticle forming processing apparatus, the outlet (outlet 4) of the processed fluid from the processing surfaces has a positive pressure over the atmospheric pressure. The processing surfaces installed facing each other have a pressure distribution, and the pressure usually drops in the direction of discharge from the processing surfaces, and the pressure approaches the atmospheric pressure at the outlet of the processed fluid. By setting the outlet of the processed fluid at a positive pressure, the residual pressure generated at the outlet of the processed fluid is counteracted, so that the processed fluid can be stably discharged. When the residual pressure remains between the processing surfaces, the processed fluid may flush due to pressure fluctuations at the processed fluid discharge part, resulting in the generation of microparticles.

<Step of Producing Approximately Spherical PLGA Microparticles>

The method of producing the approximately spherical PLGA microparticles of the present invention includes at least the step of forming particles, and may further include the step of filtration and sterilization, the step of removing a good solvent, and other steps, if necessary.

<Step of Forming Particles>

In the step of forming particles, it is preferable to use a microparticle forming apparatus in which microparticle forming is performed between a plurality of processing surfaces being capable of approaching to and separating from each other, at least one of which rotates relative to the other, which is described above. The step of forming particles is performed, for example, by continuously feeding to the microparticle forming apparatus a PLGA solution obtained by dissolving or dispersing PLGA and the biologically active substance in a good solvent of PLGA, and a solution containing a poor solvent of PLGA to prepare emulsified particles; and removing the good solvent from the produced particles to precipitate the approximately spherical PLGA microparticles of the present invention. Here, “dispersing” includes dispersing the biologically active substance as a solid in a good solvent of PLGA; emulsifying the biologically active substance in a good solvent of PLGA; forming a w/o emulsion containing an aqueous solution of a hydrophilic biologically active substance and a good solvent of PLGA; and the like.

The PLGA solution is not particularly limited as long as it is a solution in which PLGA and the biologically active substance are dissolved or dispersed in a good solvent of PLGA, and may be appropriately selected according to the intended purpose. The good solvent is not particularly limited, and may be appropriately selected according to the intended purpose. The good solvent includes, for example, a halogenated aliphatic hydrocarbon, an aliphatic ester, an alcohol, a ketone, an ether, acetonitrile, and the like. An example of the halogenated aliphatic hydrocarbon includes dichloromethane, chloroform, carbon tetrachloride, chloroethane, 2,2,2-trichloroethane, and the like. An example of the aliphatic ester includes ethyl acetate, propyl acetate, butyl acetate, and the like. An example of the alcohol includes an alcohol having low solubility in water such as benzyl alcohol, phenyl alcohol, n-butanol, and the like. An example of the ketone includes a ketone having 3 to 6 carbon atoms (e.g., acetone, methyl ethyl ketone, methyl isobutyl ketone, cyclohexanone, etc.), and the like. An example of the ether includes an ether having 2 to 6 carbon atoms (e.g., dimethyl ether, methyl ethyl ether, diethyl ether, etc.), and the like. It is preferable to select a solvent having low solubility in water, from the view point of the content of the biologically active substance and for the purpose of preventing an initial burst. A good solvent is preferably a halogenated aliphatic hydrocarbon, a ketone, and a mixture thereof, more preferably dichloromethane, acetone and a mixture thereof. These may be used alone or in combination of two kinds or more thereof. The particle diameter can be controlled by changing a kind of the solvent or a mixing amount of the solvent.

A good solvent means a solvent having high solubility of PLGA, and a poor solvent means a solvent having low or no solubility of PLGA. A good solvent and a poor solvent can be defined by, for example, a quantity of PLGA which can be dissolved in 100 g of the solvent at 25° C. In the present invention, the good solvent is preferably a solvent which dissolves 0.1 g or more, more preferably 0.2 g or more, and still more preferably 0.5 g or more of PLGA. The poor solvent is preferably a solvent which dissolves only 0.05 g or less, more preferably 0.02 g or less, and still more preferably 0.01 g or less of PLGA. The poor solvent is not particularly limited, and may be appropriately selected according to the intended purpose, and water is preferable.

A content of PLGA in a PLGA solution may be changed depending on the good solvent, depending on the particle diameter of the intended PLGA microparticles. The content of PLGA is, for example, 1 to 30% by mass, preferably 3 to 20% by mass, and more preferably 5 to 15% by mass. The content of the biologically active substance in the PLGA solution may be appropriately changed according to the intended purpose, the pharmacological effect and the like.

A stabilizer may be added to the poor solvent for further ensuring stability of the produced PLGA microparticles. The stabilizer is not particularly limited, and may be appropriately selected according to the intended purpose. The stabilizer includes, for example, polyvinyl alcohol (PVA), polyvinyl pyrrolidone (PVP), carboxy methylcellulose (CMC), hydroxypropylcellulose (HPC), hydroxypropylmethylcellulose (HPMC), lecithin, Polysorbate 80, and the like, and polyvinyl alcohol (PVA) is preferable. Further, the concentration of the added stabilizer is preferably 0.01 to 20% by mass, more preferably 5% by mass or less. The preferable poor solvent is, for example, an aqueous solution of PVA, and the like.

The PLGA solution and the solution of a poor solvent is desirably prepared using a preparation apparatus such as a rotatory dispersing apparatus which realizes uniform mixing by applying a shearing force to a fluid, for example, by rotating a stirring bar of various shapes such as a rod, a plate and a propeller in a tank, or by equipping with a screen rotating relative to a stirring bar. A stirring apparatus disclosed in JP 5147091 may be applied as a preferable example of the rotatory dispersing apparatus.

The rotatory dispersing apparatus may be a batch type one or a continuous type one. When performed by a continuous type rotatory dispersing apparatus, a stirring energy can be appropriately controlled, by using an apparatus to continuously supply and discharge a fluid to and from the stirring tank, or using a continuous mixer without using a stirring tank, or using a known stirring apparatus or a stirring means. Incidentally, the stirring energy is described in detail in JP H04-114725 by the present applicant. The stirring method in the present invention is not particularly limited, but may be performed using a various shearing type, friction type, high-pressure jet type, ultrasonic type, etc, of a stirrer, a dissolver, an emulsifier, a disperser, a homogenizer, or the like. An example thereof includes a continuous type emulsifier such as ULTRA-TURRAX (IKA-Werke GmbH & Co. KG), POLYTRON (Kinematica AG), TK HOMOMIXER (Primix Corporation), Ebara Milder (Ebara Corporation), TK HOMOMETIC LINE FLOW (Primix Corporation), Colloid Mill (Kobelko Eco-Solutions, Co., Ltd.), Slasher (NIPPON COKE & ENGINEERING, Co., Ltd.), Trigonal Wet Pulverizer (Mitsui Miike Chemical Engineering Machinery, Co., Ltd.), Cavitron (Euro Tech, Co., Ltd.), Fine Flow Mill (Pacific Machinery & Engineering, Co., Ltd.), and the like; a batch type or continuous dual type emulsifier such as Clearmix (M. Technique Co., Ltd.), Clearmix Dissolver (M. Technique Co., Ltd.), and the like. Further, it is desirable to use a stirring apparatus equipped with a stirring blade rotating at high speed and equipped with a screen outside of the stirring blade which discharges a fluid as a jet stream from an opening of the screen, particularly, the above Clearmix (M. Technique Co., Ltd.) and Clearmix Dissolver (M. Technique Co., Ltd.).

In the above microparticle forming apparatus, it is possible to control the particle diameter and the particle diameter distribution of PLGA particles by adjusting the contact surface pressure of the rotating processing surfaces at a standstill period. As a result of experiments by the present inventors, the contact surface pressure is preferably 20 $g/cm^2$ to 250 $g/cm^2$. When the contact surface pressure is lower than 20 $g/cm^2$, the thin film is not stable and the particle diameter distribution becomes wide. When the contact surface pressure is higher than 250 $g/cm^2$, it has been found difficult to adjust the intended particle diameter. The contact surface pressure may be preferably 50 $g/cm^2$ to 200 $g/cm^2$, and more preferably 80 $g/cm^2$ to 150 $g/cm^2$.

It is preferable to prevent coalescence of the respective PLGA microparticles formed by contacting the PLGA solution with the solution containing the poor solvent. As a method of preventing the coalescence, the solution containing a poor solvent is preferably added in a tank for recovering a solution discharged fluid beforehand, and is slowly stirred. By stirring, the coalescence of the PLGA microparticles can be further suppressed. A rotatory dispersing apparatus is preferable for stirring, and Clearmix Dissolver (M. Technique Co., Ltd.) is desirable. The rotatory dispersing apparatus is not particularly limited as long as the whole solution can be made to flow mildly. When stirring is strong, the PLGA emulsified particles may break down, the distribution width may become wider.

When the biologically active substance is a lipophilic biologically active substance, the step of forming particles can be suitably performed according to the above description, and approximately spherical PLGA microparticles can be manufactured. When the biologically active substance is a hydrophilic biologically active substance, the hydrophilic biologically active substance is dispersed in a good solvent of PLGA using, for example, a dispersing agent, whereby the step of forming particles can be similarly performed to produce approximately spherical PLGA microparticles.

In addition, when the biologically active substance is a hydrophilic biologically active substance, the hydrophilic biologically active substance is dissolved in an aqueous solvent such as water together with a stabilizer, if necessary, and is mixed with a solution in which PLGA is dissolved in a good solvent of PLGA, to prepare a w/o emulsion; and the above step of forming particles is performed using the w/o emulsion as a PLGA solution, and using the above microparticle forming apparatus. For preparing the w/o emulsion, an intermittent shaking method, a propeller type stirring apparatus, a method by a mixer using a turbine type stirring apparatus, a colloid mill method, a homogenizer method, and an ultrasonic irradiation method can be used. Using the above microparticle forming apparatus, this w/o emulsion of the PLGA solution, and a solution containing a poor solvent of PLGA are continuously added to prepare emulsified particles as a w/o/w emulsion; and the good solvent is removed from the produced particles to precipitate the approximately spherical PLGA microparticles of the present invention as microcapsules. This obtained PLGA microparticles as microcapsules may be used as it is, but it is also possible to further add an excipient (mannitol, sorbitol, lactose, glucose, etc.), redisperse the mixture, and freeze dry or spray dry the mixture, to be solidified. A more stable sustained release injection formulation can be obtained, by adding distilled water for injection or an appropriate dispersion medium to this solidified PLGA microparticles when used.

<Step of Filtration and Sterilization>

Sterile filtration of the prepared PLGA solution and the solution of a poor solvent is preferably performed prior to the step pf forming particles, if desired. The solution containing a poor solvent can be sterilized by filtration using a hydrophilic filter, and the PLGA solution containing PLGA and a biologically active substance can be sterilized by filtration using a hydrophobic filter. A bore diameter of the filters used for filtration is preferably 0.1 μm to 0.45 μm, more preferably 0.2 μm.

The above filter for sterile filtration is not particularly limited, and may be appropriately selected according to the intended purpose. For example, for sterile filtration of the solution containing a poor solvent, a hydrophilic filter such as polyvinylidene fluoride (PVDF) and polyethersulfone may be used. For sterile filtration of the PLGA solution, a hydrophobic filter such as polytetrafluoroethylene (PTFE) may be used. The filter for sterile filtration is not limited to the material described here, but it is necessary to be selected depending on adsorption of the medicine and a kind of the solvent.

<Step of Removing a Good Solvent>

In the step of removing a good solvent, a good solvent is removed from the emulsified particles containing PLGA and a biologically active substance. The step of removing a good solvent is not particularly limited, and may be appropriately selected according to the intended purpose, as long as the good solvent can be removed from the emulsified particles. The step of removing a good solvent includes, for example, a method of evaporating and removing the good solvent from the fluid, by at least one of heating the fluid with stirring, flowing a gas such as nitrogen gas on a surface of the fluid, and reducing a pressure of the fluid.

<Other Steps>

Other steps include, for example, a solvent composition preparation, a classification step, a particle cleaning step, and the like. Normally, coarse powder cut or fine powder cut is performed in the classification step, but the particles produced in the present invention do not substantially need the classification step. However, a classification step may be included just in case.

By the method of producing the approximately spherical PLGA microparticles of the present invention, it is possible to produce approximately spherical lactic acid-glycolic acid copolymer (PLGA) microparticles wherein an average volume-based particle diameter of the PLGA microparticles is 1 μm or more and 150 μm or less, and $0.1<(R.S.F.)\leq 1.7$.

EXAMPLE

Hereinafter, the present invention is explained in more detail with reference to Examples, but the present invention is not limited only to these Examples.

Example 1

<Preparation of PLGA Solution and Aqueous PVA Solution>

Three kinds of mixed solvents of dichloromethane (Kanto Chemical Co., Inc.) and acetone (Kanto Chemical Co., Inc.) were prepared at a mixing ratio (w/w) of 7:3, 1:1 and 3:7. The above three kind of mixed solvents were added to lactic acid-glycolic acid copolymer (PLGA 7520, FUJIFILM Wako Pure Chemical Corporation) so that the concentration of lactic acid-glycolic acid copolymer was 7% by mass. Lactic acid-glycolic acid copolymer was dissolved using a high-speed rotatory dispersing apparatus Clearmix Dissolver (M. Technique Co., Ltd.) to obtain three kinds of PLGA solutions. Ion exchanged water was added to polyvinyl alcohol 3,500, partially saponified type (PVA, FUJIFILM Wako Pure Chemical Corporation) so that the concentration was 1.0% by mass, and polyvinyl alcohol was dissolved using a high-speed rotatory dispersing apparatus Clearmix (M. Technique Co., Ltd.) to obtain an aqueous PVA solution. The aqueous PVA solution was added in a tank for collecting PLGA emulsified particles beforehand, and was slowly stirred to an extent that the solution surface just moved.

<Preparation of PLGA Microparticles>

The above PLGA solution and the aqueous PVA solution were mixed using the fluid processing apparatus described in JP 2011-189348. Here, the fluid processing apparatus described in JP 2011-189348 is an apparatus described in FIG. 25 of the publication, in which the second introduction opening d20 has a concentric annular shape which is surrounding the central opening of the processing surface 2 which is a ring-shaped disc. Specifically, the prepared aqueous PVA solution was introduced from the first introduction part d1 into the space between the processing surfaces 1 and 2 at about 0.04 to 0.05 MPaG, at 50 mL/min and at 30° C., and the prepared PLGA solution was introduced from the second introduction part d2 into the space between the processing surfaces 1 and 2 at about 0.5 to 0.8 MPaG, at 16 mL/min and at 30° C. at the rotation speed of the processing member 10 of 1,800 rpm (a peripheral speed 7.07 m/sec), and the aqueous PVA solution and the PLGA solution were mixed in a forced thin film to prepare PLGA emulsified particles containing the good solvent in the space between the processing surfaces 1 and 2. The pressure between the processing surfaces at this time was 27 g/cm$^2$. The fluid containing PLGA emulsified particles (hereinafter, PLGA emulsified particle dispersion) in the space between the processing surfaces 1 and 2 was discharged from the space between the processing surfaces 1 and 2 of the microparticle forming processing apparatus. The PLGA emulsified particle dispersion was collected in a recovery tank through an outer casing 61 for collecting the discharged PLGA emulsified particle dispersion.

The discharged fluid was desolvated with a nitrogen gas flow for 4 hours while stirring the discharged fluid at 200 rpm (a peripheral speed of 4.7 m/sec) using Clearmix Dissolver (M. Technique Co., Ltd.). Then, the good solvent was further removed under a reduced pressure with an evaporator to obtain a suspension containing the PLGA microparticles (PLGA microparticle suspension).

<Particle Diameter Distribution Evaluation>

The average volume-based particle diameter and R.S.F. of respective PLGA microparticles were measured by using respective PLGA microparticle suspensions obtained in Examples and Comparative Examples and by using Laser Diffraction Particle Size Analyser (SALD-7000, Shimadzu Corporation). The particle diameter distribution measurement results of the PLGA microparticles obtained in Example 1 are shown in Table 2.

TABLE 2

| | Average volume-based particle diameter [μm] | Particle diameter distribution [μm] D10 | D50 | D90 | R.S.F. | CV value | Mixing ratio of dichloromethane:aceton |
|---|---|---|---|---|---|---|---|
| Example 1-1 | 8.923 | 3.92 | 10.276 | 18.856 | 1.45 | 32.4% | 7:3 |
| Example 1-2 | 4.216 | 1.96 | 4.928 | 9.812 | 1.59 | 46.5% | 1:1 |
| Example 1-3 | 2.465 | 0.96 | 2.862 | 5.741 | 1.67 | 28.9% | 3:7 |

Example 2

<Preparation of PLGA Solution and Aqueous PVA Solution>

Dichloromethane (Kanto Chemical Co., Inc.) was added to lactic acid-glycolic acid copolymer (Resomer RG504, Evonik AG) so that the concentration was 20% by mass. Lactic acid-glycolic acid copolymer was dissolved using a high-speed rotatory dispersing apparatus Clearmix Dissolver (M. Technique Co., Ltd.) to obtain a PLGA solution. Thereafter, the solution was filtrated with a 0.2 μm air vent filter (φ 62, Merck KGaA). Ion exchanged water was added to polyvinyl alcohol (PVA, EG-40P, Nippon Synthetic Chemical Industry Co., Ltd.) so that the concentration was 1.5% by mass, and polyvinyl alcohol was dissolved using a high-speed rotatory dispersing apparatus Clearmix (M. Technique Co., Ltd.) to obtain an aqueous PVA solution. Thereafter, the solution was filtrated with a hydrophilic PVDF membrane filter (φ 47, Merck KGaA). The aqueous PVA solution was added in a tank for collecting PLGA emulsified particles beforehand, and was slowly stirred to an extent that the solution surface just moved.

<Preparation of PLGA Microparticles>

The above PLGA solution and the aqueous PVA solution were mixed using the fluid processing apparatus described in JP 2011-189348. Here, the fluid processing apparatus described in JP 2011-189348 is an apparatus described in FIG. 25 of the publication, in which the second introduction opening d20 has a concentric annular shape which is surrounding the central opening of the processing surface 2 which is a ring-shaped disc. Specifically, the prepared aqueous PVA solution was introduced from the first introduction part d1 into the space between the processing surfaces 1 and 2 at about 0.04 to 0.05 MPaG, at 50 mL/min and at 30° C., and the prepared PLGA solution was introduced from the second introduction part d2 into the space between the processing surfaces 1 and 2 at about 0.5 to 0.8 MPaG, at 16 mL/min and at 30° C. at the rotation speed of the processing member 10 of 1,800 rpm (a peripheral speed 7.07 m/sec), and the aqueous PVA solution and the PLGA solution were mixed in a forced thin film to prepare PLGA emulsified particles containing dichloromethane in the space between the processing surfaces 1 and 2. The pressure between the processing surfaces at this time was 27 g/cm$^2$. The fluid containing PLGA emulsified particles (hereinafter, PLGA emulsified particle dispersion) in the space between the processing surfaces 1 and 2 was discharged from the space between the processing surfaces 1 and 2 of the microparticle forming processing apparatus. The PLGA emulsified particle dispersion was collected in a recovery tank through an outer casing 61 for collecting the discharged PLGA emulsified particle dispersion.

Dichloromethane was removed with a nitrogen gas flow for 12 hours, while stirring the discharged fluid at 200 rpm (a peripheral speed of 4.7 m/sec) using Clearmix Dissolver (M. Technique Co., Ltd.), to obtain a suspension containing the PLGA microparticles (PLGA microparticle suspension). An average volume-based particle diameter of the obtained PLGA microparticles was 18.415 μm, and an R.S.F. of respective PLGA microparticles was 1.49.

Example 3

A PLGA microparticle suspension was prepared under the same condition as in Example 2, except that the recovery tank was pressured at 0.01 MPaG and the discharged liquid was collected while maintaining a positive pressure. An average volume-based particle diameter of the obtained PLGA microparticles was 50.655 μm, and an R.S.F. of respective PLGA microparticles was 0.99.

Example 4

A PLGA microparticle suspension was prepared under the same condition as in Example 1, except that in the condition of Example 2, the liquid feeding temperature of the aqueous PVA solution was changed to 24° C., the liquid feeding temperature of the PLGA solution was changed to 25° C., the liquid feeding flow rate was changed to 8 mL/min, and the rotation speed of the processing part 10 was changed to 1,500 rpm (a peripheral speed 3.93 m/sec). An average volume-based particle diameter of the obtained PLGA microparticles was 88.435 μm, and an R.S.F. of respective PLGA microparticles was 0.89.

Example 5

A PLGA microparticle suspension was prepared under the same condition as in Example 4, except that the pressure between the processing surfaces was changed to 87.8 g/cm$^2$. An average volume-based particle diameter of the obtained PLGA microparticles was 24.793 μm, and an R.S.F. of respective PLGA microparticles was 1.22.

Example 6

A PLGA microparticle suspension was prepared under the same condition as in Example 1, except that the rotation speed of the processing part 10 when mixing the aqueous PVA solution and the PLGA solution was changed to 5,000 rpm (a peripheral speed 19.64 m/sec). An average volume-based particle diameter of the obtained PLGA microparticles was 3.232 μm, and an R.S.F. of respective PLGA microparticles was 1.16.

Example 7

A PLGA microparticle suspension was prepared under the same condition as in Example 3, except that a PLGA solution was prepared by adding progesterone as a biologically active substance. An average volume-based particle diameter of the obtained PLGA microparticles was 48.925 μm, and an R.S.F. of respective PLGA microparticles was 0.86. Significant changes in the average volume-based particle diameter and R.S.F. were not seen, whether a biologically active substance exists or not.

Comparative Example 1

The aqueous PVA solution and the PLGA solution were prepared under the same condition as in Example 2 and were used. While stirring 300 mL of the PVA aqueous solution with Clearmix Dissolver (M. Technique Co., Ltd.) at a rotation speed of 2,000 rpm (a peripheral speed 3.14 m/sec) at 25° C., the PLGA solution was added dropwise at 8 mL/min for 6 minutes. The mixture was stirred for 5 minutes. Then, the rotation speed was changed to an extent that the solution surface just moved. Dichloromethane was removed by a nitrogen gas flow over 12 hours, to obtain a suspension containing PLGA microparticles (PLGA microparticle suspension). An average volume-based particle diameter of the obtained PLGA microparticles was 31.86 μm, and an R.S.F. of respective PLGA microparticles was 1.90.

Comparative Example 2

The aqueous PVA solution and the PLGA solution were prepared under the same condition as in Example 2 and were used. While stirring 300 mL of the PVA aqueous solution with Clearmix (M. Technique Co., Ltd.) at a rotation speed of 2,000 rpm (a peripheral speed 3.14 m/sec) at 25° C., the PLGA solution was added dropwise at 8 mL/min for 6 minutes. The mixture was stirred for 5 minutes. Then, the rotation speed was changed to an extent that the solution surface just moved. Dichloromethane was removed by a nitrogen gas flow over 12 hours, to obtain a suspension containing PLGA microparticles (PLGA microparticle suspension). An average volume-based particle diameter of the obtained PLGA microparticles was 5.353 μm, and an R.S.F. of respective PLGA microparticles was 1.81.

Comparative Example 3

The aqueous PVA solution and the PLGA solution were prepared under the same condition as in Example 2 and were used. While treating 50 mL of the aqueous PVA solution with an ultrasonic disperser GSD 50 (Ginsen Co., Ltd.), the PLGA solution was added dropwise at 8 mL/min for 1 minute. The mixture was stirred for 5 minutes. Dichloromethane was removed by a nitrogen gas flow over 12 hours to obtain a suspension containing PLGA microparticles (PLGA microparticle suspension), while the mixture was slowly stirred with a stirrer to an extent that the solution surface just moved. An average volume-based particle diameter of the obtained PLGA microparticles was 6.584 μm, and an R.S.F. of respective PLGA microparticles was 2.53.

Comparative Example 4

The aqueous PVA solution and the PLGA solution were prepared under the same condition as in Example 2 and were used. While stirring 300 mL of the aqueous PVA solution with Polytron Disperser PT 1200 E (Kinematica AG) at 25° C., the PLGA solution was added dropwise at 8 mL/min for 6 minutes. The mixture was stirred for 5 minutes. Then, the rotation speed was changed to an extent that the solution surface just moved. Dichloromethane was removed by a nitrogen gas flow over 12 hours, to obtain a suspension containing PLGA microparticles (PLGA microparticle suspension). An average volume-based particle diameter of the obtained PLGA microparticles was 8.962 μm, and an R.S.F. of respective PLGA microparticles was 3.85.

Comparative Example 5

A PLGA microparticle suspension was prepared under the same condition as in Comparative Example 3, except that the stirrer in Comparative Example 3 was changed to a homomixer HM-310 (AS ONE Corporation). An average volume-based particle diameter of the obtained PLGA microparticles was 9.126 μm, and an R.S.F. of respective PLGA microparticles was 4.38.

The particle diameters, R.S.F. and CV values of the PLGA microparticles of Examples 2 to 7 and Comparative Examples 1 to 5 are shown in Table 3.

TABLE 3

| | Average volume-based particle diameter | Particle diameter distribution [μm] | | | | CV |
|---|---|---|---|---|---|---|
| | [μm] | D10 | D50 | D90 | R.S.F. | value |
| Example 2 | 18.415 | 16.257 | 20.164 | 46.208 | 1.490 | 28.2% |
| Example 3 | 50.655 | 29.768 | 50.321 | 79.447 | 0.990 | 12.4% |

TABLE 3-continued

| | Average volume-based particle diameter | Particle diameter distribution [μm] | | | | CV |
|---|---|---|---|---|---|---|
| | [μm] | D10 | D50 | D90 | R.S.F. | value |
| Example 4 | 88.435 | 56.417 | 91.751 | 138.006 | 0.890 | 9.2% |
| Example 5 | 24.793 | 11.736 | 28.304 | 46.388 | 1.220 | 12.7% |
| Example 6 | 3.232 | 0.971 | 3.784 | 5.347 | 1.160 | 50.6% |
| Example 7 | 48.925 | 29.890 | 49.563 | 72.556 | 0.860 | 37.4% |
| Comparative Example 1 | 31.860 | 2.289 | 29.780 | 58.980 | 1.900 | 66.4% |
| Comparative Example 2 | 5.353 | 1.438 | 7.983 | 15.923 | 1.810 | 64.0% |
| Comparative Example 3 | 6.584 | 0.120 | 10.860 | 27.600 | 2.530 | 72.6% |
| Comparative Example 4 | 8.962 | 0.965 | 11.623 | 45.680 | 3.850 | 78.4% |
| Comparative Example 5 | 9.126 | 0.896 | 11.232 | 50.134 | 4.380 | 80.2% |

INDUSTRIAL APPLICABILITY

The present invention provides approximately spherical PLGA microparticles having an average volume-based particle diameter of 1 μm or more and 150 μm or less wherein there are few coarse particles or ultrafine particles without a classification step, and the particle diameter distribution is sharp around the target particle diameter; and a method capable of efficiently producing the approximately spherical PLGA microparticles.

REFERENCE SINGS LIST

1 First processing surface
2 Second processing surface
C Centrifugal force direction
R Rotation direction
g Reference line
10 First processing part
13 Recess
16 Flat surface
20 Second processing part
d1 First introduction part
d2 Second introduction part
d10 First introduction opening
d20 Second introduction opening

The invention claimed is:

1. A method of producing approximately spherical lactic acid-glycolic acid copolymer (PLGA) microparticles comprising a biologically active substance, using a processing apparatus in which microparticle forming is performed between the processing surfaces being capable of approaching to and separating from each other at least one of which rotates relative to the other, which comprises a step of forming microparticles in which the approximately spherical PLGA microparticles are formed by continuously introducing into the processing apparatus, a PLGA solution obtained by dissolving or dispersing PLGA and the biologically active substance in a good solvent of PLGA and a solution containing a poor solvent of PLGA, are continuously introduced into a minute distance of 1 mm or less between processing surfaces of a processing apparatus in which pulverization is performed between the processing surfaces being capable of approaching to and separating from each other at least one of which rotates relative to the other; and the approximately spherical PLGA microparticles are formed in the thin film fluid formed in the space between the processing surfaces without a classification step, and wherein the good solvent of PLGA is a solvent which dissolves 0.1 g or more of PLGA in 100 g of the solvent at 25° C., and the poor solvent of PLGA is a solvent which dissolves 0.05 g or less of PLGA in 100 g of the solvent at 25° C., wherein an average volume-based particle diameter of the PLGA microparticles is 1 μm or more and 150 μm or less, and a Reactive Span Factor (R.S.F.) of the PLGA microparticles is satisfied with formula (1):

$$0.1 < (R.S.F) \leq 1.7 \quad \text{formula (1)}$$

wherein an R.S.F. means (D90−D10)/D50,

D90 is a particle diameter (μm) corresponding to the cumulative 90% by volume of the cumulative particle diameter distribution from the small particle side, D50 is a particle diameter (μm) corresponding to the cumulative 50% by volume of the cumulative particle diameter distribution from the small particle side, and D10 is a particle diameter (μm) corresponding to the cumulative 10% by volume of the cumulative particle diameter distribution from the small particle side.

2. The method of producing the approximately spherical PLGA microparticles according to claim 1, wherein when microparticle forming is performed using the processing apparatus, the outlet of the processed fluid from the processing surfaces has a positive pressure over the atmospheric pressure.

3. The method of producing the approximately spherical PLGA microparticles according to claim 1, wherein the surface pressure in a shut down period of the processing surfaces being capable of approaching to and separating from each other at least one of which rotates relative to the other in the processing apparatus is 20 g/cm$^2$ to 250 g/cm$^2$.

4. The method of producing the approximately spherical PLGA microparticles according to claim 1, wherein the PLGA solution and the solution containing the poor solvent are respectively aseptically filtered, and then the approximately spherical PLGA microparticles are produced in an aseptic environment.

5. The method of producing the approximately spherical PLGA microparticles according to claim 1, wherein the biologically active substance is a lipophilic biologically active substance.

* * * * *